United States Patent [19]

Miller

[11] Patent Number: 5,206,369

[45] Date of Patent: Apr. 27, 1993

[54] PROCESS FOR THE DEHYDRATION OF DIHYDROXYPIPERIDINEDICARBOXYLATES

[75] Inventor: William H. Miller, Glendale, Mo.

[73] Assignee: Monsanto Company, St. Louis, Mo.

[21] Appl. No.: 822,791

[22] Filed: Jan. 21, 1992

[51] Int. Cl.$^5$ .......................................... C07D 211/02
[52] U.S. Cl. .................................................. 546/249
[58] Field of Search ......................................... 546/249

[56] References Cited

U.S. PATENT DOCUMENTS 4,692,184 9/1987 Lee .
4,908,057 3/1990 Chupp et al. .
4,908,398 3/1990 Li Bossi et al. ............... 546/249
5,051,512 9/1991 Baysdon et al. .

Primary Examiner—Marianne M. Cintins
Assistant Examiner—John Peabody
Attorney, Agent, or Firm—Grace L. Bonner; Howard C. Stanley

[57] ABSTRACT

An improved process for dehydrating dialkyl 2,6-bis(trifluoromethyl)-2,6-dihydroxy-4-(alkyl)-3,5-piperidinedicarboxylates using concentrated sulfuric acid essentially in the absence of a solvent to prepare the corresponding dialkyl 2,6-bis(trifluoromethyl)dihydro-4-(alkyl)-3,5-pyridinedicarboxylates.

5 Claims, No Drawings

PROCESS FOR THE DEHYDRATION OF DIHYDROXYPIPERIDINEDICARBOXYLATES

FIELD OF THE INVENTION

The present invention provides an improved process for the dehydration of dihydroxypiperidinedicarboxylates to produce dihydropyridinedicarboxylates.

BACKGROUND OF THE INVENTION

It is well known that dihydroxypiperidines may be dehydrated to produce dihyropyridines by the use of an acid or an anhydride. U.S. Pat. No. 4,692,184 (Lee, 9/87) discloses several agents and the conditions under which they were used to produce various fluorinated dihydropyridinedicarboxylates which were in turn used to produce herbicidal fluorinated pyridinedicarboxylates, including dithiopyr. Example GG therein discloses the dehydration of dimethyl 2,6-bis(trifluoromethyl)-2,6-dihydroxy-4-(2-methylpropyl)-3,5-piperidinedicarboxylate using concentrated sulfuric acid in methylene chloride at <10 C. In this example, sulfuric acid is used at the molar ratio of 32.6 moles per mole of dihydroxypiperidine. Example HH of '184 discloses dehydration of trans-diethyl 2,6-bis(difluoromethyl)-2,6-dihydroxy-4-(2-methylpropyl)-3,5-piperidinedicarboxylate using excess trifluoroacetic anhydride at ambient temperatures up to 36° C. Example II of '184 discloses dehydration of diethyl 2,6-bis(trifluoromethyl)-2,6-dihydroxy-4-(2-thienyl)-3,5-piperidinedicarboxylate using p-toluenesulfonic acid in toluene under reflux conditions.

In U.S. Pat. No. 4,908,057 (Chupp 3/90), the reaction disclosed in Example GG of '184 is reported as being performed in toluene.

In U.S. Pat. No. 5,051,512 (Baysdon, 9/91), a process for the dehydration of the thiol ester analogs, dihydroxypiperidinedicarbothioates, is disclosed. The dehydration agent is hydrogen chloride or aqueous hydrochloric acid. The reaction is run at about 80° C., preferably with no solvent present.

However, none of the previously reported dehydration procedures provide a high-yielding, cost-effective process with minimal by-product formation and minimal waste stream production for the conversion of dihydroxypiperidinedicarboxylates to dihydropyridinedicarboxylates. It is an object of the present invention to provide such a process. It is a further object of the present invention to provide such a process requiring a reduced amount of dehydration agent.

SUMMARY OF THE INVENTION

The present invention provides a process for dehydrating a dialkyl 2,6-bis(trifluoromethyl)-2,6-dihydroxy-4-(alkyl)-3,5-piperidinedicarboxylate to prepare the corresponding dialkyl 2,6-bis(trifluoromethyl)-dihydro-4-(alkyl)-3,5pyridinedicarboxylates comprising contacting said dihydroxypiperidine with concentrated sulfuric acid, in a molar ratio between about 1.5 and about 2.2 moles per mole of dihydroxypiperidine, at a temperature at which the dihydroxypiperidine or mixture containing it is substantially liquid and essentially in the absence of a solvent. This temperature is generally between about 55° and about 90 ° C., preferably between 65° and 75° C. The molar ratio of acid is preferably between about 1.7 and about 1.9 moles per mole of dihydroxypiperidine.

The reaction produces a mixture of the isomers of dihydropyridinedicarboxylate, which may then be converted to the desired pyridine by dehydrofluorination.

An advantage of this process is that a reduced amount of sulfuric acid is needed as compared to the lower temperature reaction carried out in the presence of a solvent. A further advantage is a more complete reaction with a reduced amount of decomposition products, as compared to other dehydrating agents. These advantages result in reduced energy and capital equipment costs compared to prior low temperature reactions; reduced materials cost by reduction in acid and elimination of solvent; reduced waste disposal costs for the solvent; and a higher quality product having reduced numbers of impurities, not achievable with the current technology.

DETAILED DESCRIPTION OF THE INVENTION

Various dialkyl 2,6-bis(trifluoromethyl)-2,6-dihydroxy-4-(alkyl)-3,5-piperidinedicarboxylates useful in the present process may be prepared as described in Lee '184, which is herein incorporated by reference. The following examples were carried out with diethyl 2,6-bis(trifluoromethyl)-2,6-dihydroxy-4-(2-methylpropyl)-3,5-piperidinedicarboxylate, which is described in Example Q therein, or, for comparison, with the methyl thiol ester analog, S,S-methyl 2,6-bis(trifluoromethyl)-2,6-dihydroxy-4-(2-methylpropyl)3,5-piperidinedicarbothioate, described in Baysdon '512, herein incorporated by reference.

As used herein, the term "alkyl" means a straight- or branched-chain alkyl group having from 1 to 6 carbon atoms.

Solventless dehydration reactions are known to have advantages such as lower raw material costs and possibly reduced waste production. In Baysdon '512, such a process was disclosed for the thiol ester analogs of the dihydroxypiperidinedicarboxylates of the present invention, as discussed above. However, when a process such as described in '512 was used for the oxy ester compound, unacceptably low yields were seen. See Comparative Examples 1–4 below.

It was also found that solventless dehydration of the thiol ester analogs was not successful using the present invention process conditions. An unacceptably high level of decomposition was found. See Comparative Example 5 below.

Surprisingly, it has been found that concentrated sulfuric acid may be used for the dehydration of dihydroxypiperidinedicarboxylates when the amount of acid is greatly reduced and the temperature is raised to about the melting point of the crude substrate. These changes allow for the exclusion of solvents necessary for the low temperature reaction. An optimized low temperature reaction required at least 4.7 moles sulfuric acid per mole of substrate. The present invention uses only about 1.5 to 2.2 moles acid per mole of substrate, preferably only about 1.7 to 1.9.

The reaction is carried out at a temperature at which the crude substrate is liquid or substantially liquid. At this temperature some impurities including water are driven off. As the mixture becomes more pure the substrate may begin to crystalize. However, the reaction can be successfully carried out in a slurry of the substrate. Thus the reaction temperature can be slightly below the melting point of the pure substrate, which is generally between 60° and 85° C. For the compound diethyl 2,6-bis(trifluoromethyl)-2,6-dihydroxy-4-(2-methylpropyl)-3,5-piperidinedicarboxylate, produced by the Hantzsch reaction described in Lee '184, the melting point of the crude substrate can be as high as 76° to 78° C., but the reaction can be carried out effectively at temperatures as low as 65° to 70° C.

Water may be added to the completed reaction to remove excess acid and salts before proceeding to the next step in the manufacturing process. As shown in Example 6, this reaction produces a dihydropyridine product in high yields with relatively lower levels of intermediates and decomposition products, described below.

As can be seen from the following examples, solventless dehydration of dialkyl 2,6-bis(trifluoromethyl)-2,6-dihydroxy-4-(alkyl)-3,5-piperidinedicarboxylate using concentrated sulfuric acid provides a surprisingly high yield of dialkyl 2,6-bis(trifluoromethyl)-dihydro-4-(alkyl)-3,5-pyridinedicarboxylates, with comparatively little decomposition or incomplete reaction products. This highly advantageous process provides a means of producing an intermediate for dithiopyr with reduced energy costs, reduced raw material costs, reduced waste, and reduced processing time, with the result being greatly increased processing efficiency.

COMPARATIVE EXAMPLES 1-4

The four reactions were carried out by adding 3.9 moles of HCl (30%) (Example 4 used dry HCl) to a crude dihydroxypiperidine substrate (the methyl thiol diester or the ethyl oxy diester) and heating to the reaction temperature indicated. The reaction mixture was held at that temperature and stirred for 2 to 4 hours. The crude product was analyzed by GC and the yield of desired dihydropyridinedicarboxylates (DHP) was calculated along with the level of intermediates (INT), which are formed by the incomplete dehydration, and of decomposition products, which are decarboxylated materials (DECARB). The results are reported in Table 1.

COMPARATIVE EXAMPLE 5

The methyl thio dihydroxypiperidine compound described in '512 was treated with concentrated $H_2SO_4$ in a molar ratio of 1.7 moles per mole of substrate, and held at 65°-70° C. for 0.3 hours. The dihydropyridine crude product was analyzed as described for Examples 1-4. The results are reported in Table 1.

EXAMPLE 6

The crude reaction mixture produced by the process described in '184, containing diethyl 2,6-bis(trifluoromethyl)-2,6-dihydroxy-4-(2-methylpropyl) 3,5-piperidinedicarboxylate (125 g) was maintained at 65°-70° C. and exposed to reduced pressure (120 mm) for 30-40 min to remove water and other volatile compounds. As impurities were removed, the temperature was raised to 76°-78° C. to keep the mixture fluid. Concentrated $H_2SO_4$ (40 g, a molar ratio of 1.7 moles acid per mole of dihydroxypiperidine) was added via an addition funnel over 3 min, while heating was continued to keep the reaction mixture at 76°-78 C. The mixture was held at that temperature for 15 min and then was allowed to cool to 65° C. for 15 min. Water (29 mL) was added over 3-5 min, the mixture was allowed to settle, and the aqueous phase was removed, all the while maintaining the temperature at 65°-70° C. The resulting product was analyzed as described in Examples 1-4 and the results are given in Table 1.

TABLE 1

| | Ester Substrate | Temp (°C.) | Reaction Yield (Percent) | | |
|---|---|---|---|---|---|
| | | | INT | DHP | DECARB |
| 1 | Methyl Thio | 80 | — | 67.2 | 0.7 |
| 2 | Ethyl Oxy | 75 | 9 | 83 | — |
| 3 | " | 80 | 8.6 | 75 | — |
| 4 | " | 70 | 6.9 | 81.8 | 2.6 |
| 5 | Methyl Thio | 65-70 | — | 70.9 | 8.3 |
| 6 | Ethyl Oxy | 76-78 | 2.3 | 94.1 | 1.2 |

What is claimed is:

1. A process for dehydrating a dialkyl 2,6-bis(trifluoromethyl)-2,6-dihydroxy-4-(alkyl)-3,5-piperidinedicarboxylate to prepare the corresponding dialkyl 2,6-bis(trifluoromethyl)dihydro-4-(alkyl)-3,5-pyridinedicarboxylates comprising contacting the dihydroxypiperidine starting material with concentrated sulfuric acid, in a molar ratio between about 1.5 and about 2.2 moles of the acid per mole of dihydroxypiperidine, at a temperature at which the dihydroxypiperidine or mixture containing it is substantially liquid, and essentially in the absence of a solvent for the dihydroxypiperidine.

2. The process of claim 1 wherein the temperature is between about 55° and about 90 ° C.

3. The process of claim 2 wherein the temperature is between about 65° and about 75° C.

4. The process of claim 3 wherein said molar ratio is between about 1.7 and about 1.9.

5. The process of claim 4 wherein the dihydroxypiperidine is diethyl 2,6-bis(trifluoromethyl)-2,6-dihydroxy-4-(2-methylpropyl)-3,5-piperidinedicarboxylate.

* * * * *